(12) United States Patent
Eskuri

(10) Patent No.: US 10,029,076 B2
(45) Date of Patent: Jul. 24, 2018

(54) INTRAVASCULAR GUIDEWIRE

(75) Inventor: Alan Eskuri, Irvine, CA (US)

(73) Assignee: Covidien LP, Mansfield, MA (US)

( * ) Notice: Subject to any disclaimer, the term of this patent is extended or adjusted under 35 U.S.C. 154(b) by 940 days.

(21) Appl. No.: 13/407,182

(22) Filed: Feb. 28, 2012

(65) Prior Publication Data

US 2013/0226033 A1    Aug. 29, 2013

(51) Int. Cl.
  *A61M 25/00*    (2006.01)
  *A61M 25/09*    (2006.01)

(52) U.S. Cl.
  CPC ... *A61M 25/09* (2013.01); *A61M 2025/09083* (2013.01); *A61M 2025/09091* (2013.01); *A61M 2025/09133* (2013.01)

(58) Field of Classification Search
  USPC .................................. 600/585; 604/164.13
  See application file for complete search history.

(56) References Cited

U.S. PATENT DOCUMENTS

| | | |
|---|---|---|
| 5,234,003 A | 8/1993 | Hall |
| 5,243,996 A | 9/1993 | Hall |
| 5,341,818 A | 8/1994 | Abrams et al. |
| 5,365,943 A | 11/1994 | Jansen |
| 5,433,200 A | 7/1995 | Fleischhacker, Jr. |
| 5,606,981 A | 3/1997 | Tartacower et al. |
| 5,666,969 A | 9/1997 | Urick et al. |
| 5,682,894 A | 11/1997 | Orr et al. |
| 5,807,279 A | 9/1998 | Viera |
| 5,865,767 A | 2/1999 | Frechette et al. |
| 5,865,768 A | 2/1999 | Orr |
| 5,885,227 A | 3/1999 | Finlayson |
| 5,916,178 A | 6/1999 | Noone et al. |
| 6,039,699 A | 3/2000 | Viera |
| 6,068,623 A | 3/2000 | Zadno-Azizi et al. |

(Continued)

FOREIGN PATENT DOCUMENTS

| | | |
|---|---|---|
| CN | 101618249 A | 1/2010 |
| EP | 1 391 216 A1 | 2/2004 |

(Continued)

OTHER PUBLICATIONS

European Search Report dated Jul. 30, 2013 from counterpart European Application No. 13156588.9 (13 pgs.).

(Continued)

*Primary Examiner* — Daniel Cerioni
(74) *Attorney, Agent, or Firm* — Shumaker & Sieffert, P.A.

(57) ABSTRACT

A guidewire for use in a medical procedure includes an elongate guide member dimensioned for insertion within a body vessel of a subject. The guide member defines a longitudinal axis and has trailing and leading end segments. The leading end segment has a reduced cross-sectional dimension relative to a cross-sectional dimension of the trailing end segment. The leading end segment includes a first core element comprising a first material and a second core element comprising a second material different from the first material and being forward of the first core element. The first material of the first core element has greater rigidity than the rigidity of the second material of the second core element, to thereby facilitate advancement of, and application of torque to, the leading end segment while minimizing deformation.

20 Claims, 3 Drawing Sheets

(56) References Cited

U.S. PATENT DOCUMENTS

| | | | |
|---|---|---|---|
| 6,329,069 B1* | 12/2001 | Azizi et al. | ............ 428/600 |
| 6,488,637 B1 | 12/2002 | Eder et al. | |
| 6,491,648 B1 | 12/2002 | Cornish et al. | |
| 6,592,570 B2 | 7/2003 | Abrams et al. | |
| 6,602,228 B2 | 8/2003 | Nanis et al. | |
| 6,875,949 B2 | 4/2005 | Hall | |
| 6,908,443 B2 | 6/2005 | Burmeister et al. | |
| 7,214,201 B2 | 5/2007 | Burmeister et al. | |
| 7,252,643 B2 | 8/2007 | Fujimoto et al. | |
| 7,316,656 B2 | 1/2008 | Shireman et al. | |
| 7,540,845 B2 | 6/2009 | Parins | |
| 7,632,237 B2 | 12/2009 | Murayama et al. | |
| 7,637,875 B2 | 12/2009 | Itou | |
| 7,699,792 B2 | 4/2010 | Hofmann et al. | |
| 7,715,903 B2 | 5/2010 | Hartley et al. | |
| 7,722,551 B2 | 5/2010 | Murayama et al. | |
| 7,722,552 B2 | 5/2010 | Aimi et al. | |
| 7,762,962 B2 | 7/2010 | Mishima | |
| 7,955,272 B2 | 6/2011 | Rooney et al. | |
| 8,007,447 B2 | 8/2011 | Murayama et al. | |
| 2001/0009980 A1 | 7/2001 | Richardson et al. | |
| 2003/0000757 A1 | 1/2003 | Ishida et al. | |
| 2003/0216668 A1 | 11/2003 | Howland et al. | |
| 2004/0064069 A1 | 4/2004 | Reynolds et al. | |
| 2004/0106878 A1 | 6/2004 | Skujins et al. | |
| 2004/0167438 A1 | 8/2004 | Sharrow | |
| 2004/0167441 A1 | 8/2004 | Reynolds et al. | |
| 2007/0232957 A1 | 10/2007 | Murayama et al. | |
| 2007/0244414 A1 | 10/2007 | Reynolds et al. | |
| 2007/0265553 A1 | 11/2007 | Murayama et al. | |
| 2008/0161726 A1 | 7/2008 | Itou | |
| 2008/0161728 A1 | 7/2008 | Mishima | |
| 2008/0171217 A1 | 7/2008 | Mishima | |
| 2008/0171952 A1 | 7/2008 | Mishima | |
| 2008/0183182 A1 | 7/2008 | Satou et al. | |
| 2008/0200879 A1 | 8/2008 | Jalisi et al. | |
| 2008/0214959 A1 | 9/2008 | Miyata et al. | |
| 2008/0234606 A1 | 9/2008 | Yutaka | |
| 2008/0269641 A1 | 10/2008 | O'Shaughnessy et al. | |
| 2009/0005706 A1 | 1/2009 | Miyata et al. | |
| 2009/0076416 A1 | 3/2009 | Treacy et al. | |
| 2009/0118675 A1 | 5/2009 | Czyscon et al. | |
| 2009/0182246 A1 | 7/2009 | Kinoshita et al. | |
| 2010/0004562 A1 | 1/2010 | Jalisi et al. | |
| 2010/0286566 A1 | 11/2010 | Griffin et al. | |
| 2011/0230862 A1 | 9/2011 | Segner et al. | |
| 2011/0257622 A1 | 10/2011 | Salahieh et al. | |

FOREIGN PATENT DOCUMENTS

| | | |
|---|---|---|
| EP | 1388349 A1 | 2/2004 |
| EP | 1 498 152 A1 | 1/2005 |
| EP | 1 543 857 A1 | 6/2005 |
| EP | 1 576 980 A1 | 9/2005 |
| EP | 1944053 A1 | 7/2008 |
| EP | 2 005 988 A1 | 12/2008 |
| EP | 2 140 904 A1 | 1/2010 |
| JP | 2008161491 A | 7/2008 |
| JP | 2008161588 A | 7/2008 |

OTHER PUBLICATIONS

Notice of Final Rejection, and translation thereof, from counterpart Japanese Patent Application No. 2013-037291, dated Jul. 24, 2014, 7 pp.

Examiner's Report from Counterpart Canadian Patent Application No. 2,806,985, dated Apr. 29, 2014, 3 pp.

First Office Action, and translation thereof, from counterpart Chinese Patent Application No. 201310165105.8, dated Jul. 7, 2014, 18 pp.

Office Action of the Substantive Examination, and translation thereof, from counterpart Russian Patent Application No. 2013108351/14(012390) dated Jul. 20, 2014, 9 pp.

Examiner's Report from counterpart Canadian Patent Application No. 2806985, dated Jan. 20, 2015, 4 pp.

Notice of Final Rejection, and translation thereof, from counterpart Korean Application No. 10-2013-0021901, dated Apr. 24, 2015, 7 pp.

Rejection Decision, and translation thereof, from counterpart Chinese Application No. 201310165105.8, dated Aug. 12, 2015, 14 pp.

Notification of the Second Office Action, and translation thereof, from counterpart Chinese Patent Application No. 201310165105.8, dated Mar. 30, 2015, 19 pp.

Notice of Reasons for Rejection, and translation thereof, from counterpart Japanese Application No. 2013-37291, dated Oct. 19, 2015, 7 pp.

Notice of Preliminary Rejection, and translation thereof, from counterpart Korean Application No. 10-2013-0021901, dated Jun. 18, 2014, 11 pp.

Notice of Last Preliminary Rejection, and translation thereof, from counterpart Korean Application No. 10-2013-21901, dated Aug. 25, 2015, 9 pp.

Decision of Second Final Rejection, and English Translation thereof, from counterpart Korean Patent Application No. 10-2013-0021901, dated Feb. 26, 2016, 5 pp.

Notification of Reexamination, and translation thereof, from counterpart Chinese Application No. 201310165105.8 dated May 5, 2017, 13 pp.

The Notification of Reexamination, and translation thereof, from counterpart Chinese Application No. 201310165105.8, dated Sep. 20, 2016, 19 pp.

* cited by examiner

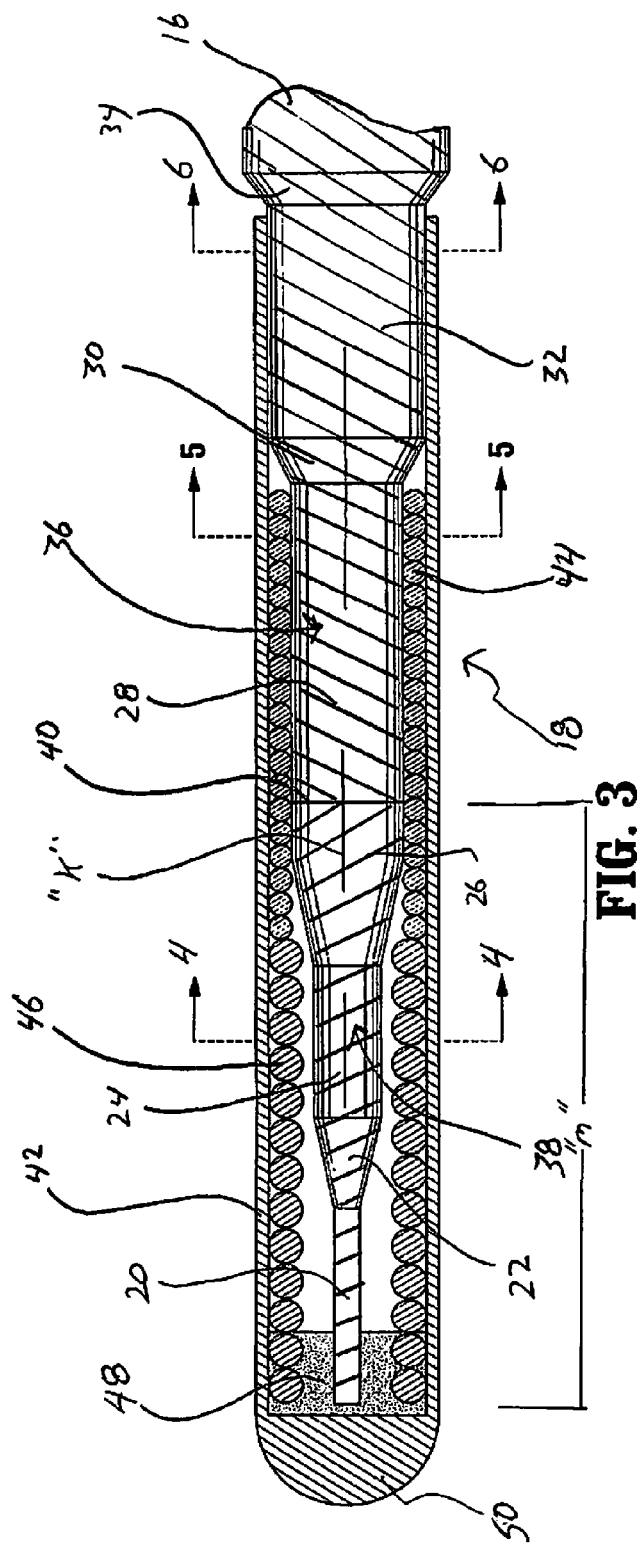
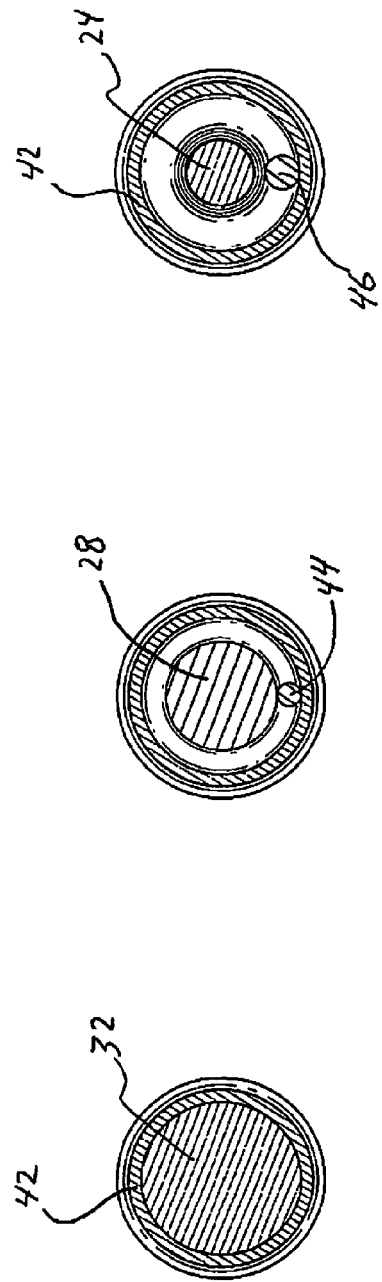
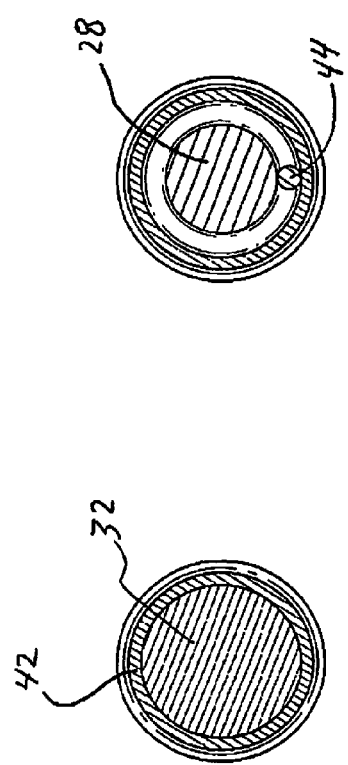
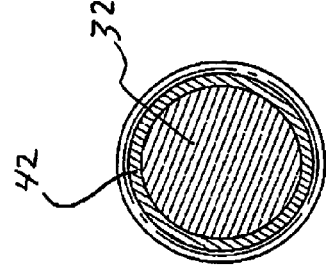

INTRAVASCULAR GUIDEWIRE

BACKGROUND

1. Technical Field

The present disclosure generally relates to intravascular devices, and, in particular, relates to an intravascular guidewire for assisting in placement of an intravascular device within, e.g., the neurovascular space, for facilitating diagnostic and/or therapeutic neurovascular procedures.

2. Description of Related Art

The effectiveness of an intravascular guidewire in advancing through tortuous vasculature without undesired deformation or kinking is dependent upon a number of factors and design considerations. These factors include, inter-alia, the material(s) of fabrication of the guidewire, guidewire dimensions and intended use. Generally, a balance must be achieved to provide the required torsional, lateral, tensile and/or column strengths to enable easy and precise manipulation and steerability in the tortuous vasculature. Guidewires for neurovascular intravascular procedures face additional challenges due to the relatively small diameter required to navigate through the narrow and remote locations of the neurovasculature space.

SUMMARY

Accordingly, the present disclosure is directed to a guidewire capable of accessing distal reaches of the vasculature, including the neurovasculature, while exhibiting sufficient torsional and lateral stiffness to enable steering of the guidewire through these tortuous regions. What is also desired is a guidewire having a distal end with improved tensile and torsional integrity, yet with the capability to readily bend in any direction.

In accordance with one embodiment of the present disclosure, a guidewire for use in a medical procedure includes an elongate guide member dimensioned for insertion within a body vessel of a subject. The guide member defines a longitudinal axis and has trailing and leading end segments. The leading end segment has a reduced cross-sectional dimension relative to a cross-sectional dimension of the trailing end segment. The leading end segment includes a first core element comprising a first material and a second core element comprising a second material different from the first material and being forward of the first core element. The first material of the first core element has greater rigidity than the rigidity of the second material of the second core element, to thereby facilitate advancement of, and application of torque to, the leading end segment while minimizing deformation. The first material of the first core element may comprise a nickel-cobalt-chromium alloy or, alternatively, stainless steel. The second material of the second core element may comprise nickel-titanium or an alloy thereof. The first core element may be directly bonded to the second core element through, e.g., a welding process, which may be devoid of any filler material.

A coil member may be coaxially mounted about the guide member and dimensioned to longitudinally extend to at least partially encompass the first and second core elements. The coil member may include a first coil segment and a second coil segment forward of the first coil segment. The first coil segment may comprise a first coil material and the second coil segment may comprise a second coil material different from the first coil material. The first coil segment may have a first torsional strength and the second coil segment may have a second torsional strength greater than the first torsional strength. The second coil segment may be required to assume a greater torsional load to compensate for, e.g., a reduced cross sectional dimension adjacent the tip of the guide member.

The leading end segment may include at least two tapered segments obliquely arranged with respect to the longitudinal axis. In one embodiment, the leading end segment includes, from leading to trailing: a remote segment; a first tapered segment extending from the first remote segment and coterminous therewith; a first generally annular segment extending from the first tapered segment and coterminous therewith; a second tapered segment extending from the second generally annular segment and coterminous therewith; and a second generally annular segment extending from the second tapered segment and coterminous therewith. In embodiments, the first core element is connected to the second core element within the second generally annular segment or may be connected within the third generally annular segment.

A sleeve may be mounted over at least a major portion of the leading end segment. The sleeve may comprise polyurethane and tungsten material. The sleeve also may define an arcuate distal tip.

BRIEF DESCRIPTION OF THE DRAWINGS

Embodiments of the present disclosure will be readily appreciated by reference to the drawings wherein:

FIG. 3 is a side cross-sectional view of the leading end segment of the guide member of the guidewire of FIGS. 1 and 2;

FIG. 4 is a cross-sectional view of the guide member of the guidewire taken along the lines 4-4 of FIG. 3;

FIG. 5 is a cross-sectional view of the guide member of the guidewire taken along the lines 5-5 of FIG. 3; and FIG. 6 is a cross-sectional view of the guide member of the guidewire taken along the lines 6-6 of FIG. 3.

DESCRIPTION

Figure 1:
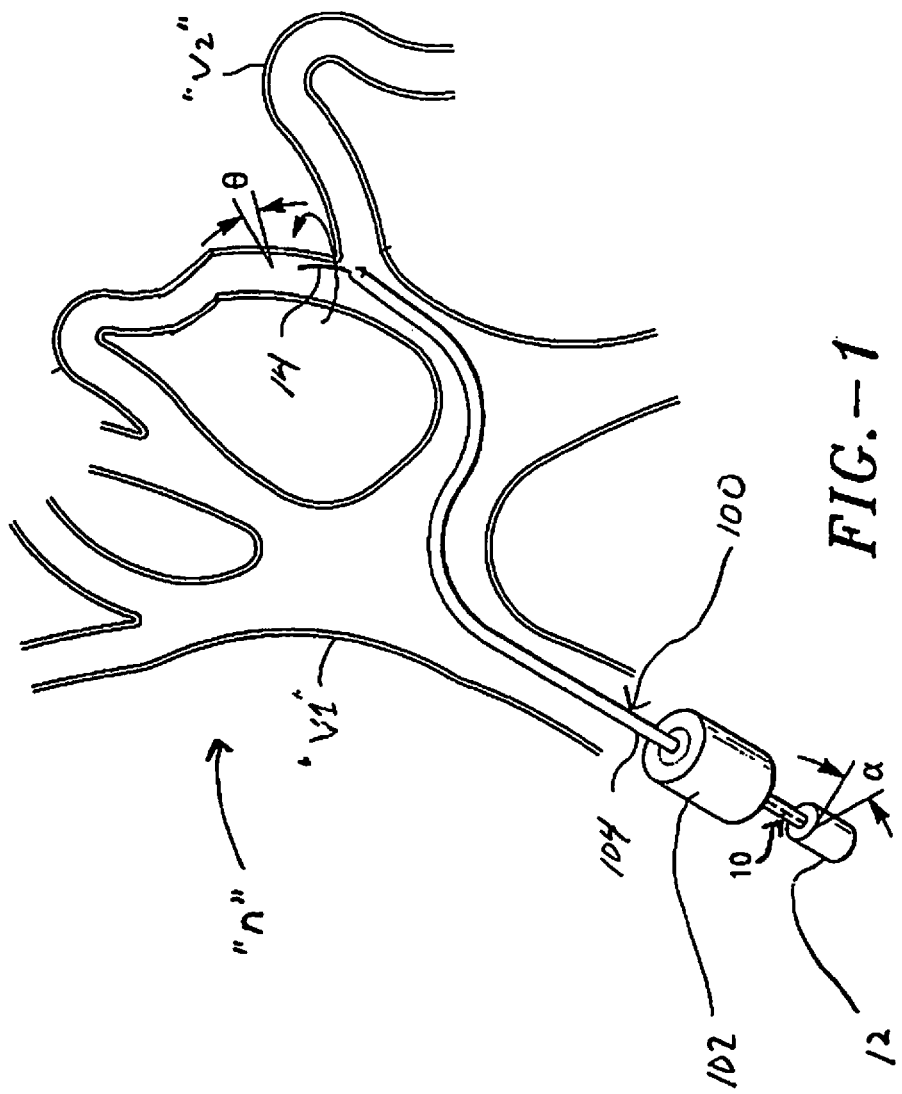
FIG. 1 is a perspective view of a guidewire and catheter in use within a tortuous region of the vasculature of a patient in accordance with the principles of the present disclosure.

In the following description, the terms "proximal" and "distal" as used herein refer to the relative position of the guidewire in a lumen. The "proximal" or "trailing" end of the guidewire is the guidewire segment extending outside the body closest to the clinician. The "distal" or "leading" end of the guidewire is the guidewire segment placed farthest into a body lumen from the entrance site.

The guidewire of the present disclosure has particular application in a neurovascular procedure, but may be used in any interventional, diagnostic, and/or therapeutic procedure including coronary vascular, peripheral vascular, and gastrointestinal applications in addition to a neurovascular application.

In the figures below, the full length of the guidewire is not shown. The length of the guidewire can vary depending on the type of interventional procedure, though typically it ranges in length from 30 to 400 centimeters (cm). Common lengths of guidewires for coronary, peripheral and neurovascular interventions may range from 170 to 300 cm in length. These lengths permit the use of standardized rapid exchange or over-the-wire catheter systems. The length of the shaped distal end also may vary, for example, from about 5 to about 80 cm in length.

In accordance with one application of the present disclosure, the maximum outer diameter of the guidewire ranges from about 0.008 inches to about 0.018 inches. These diameters are standard for guidewires used, e.g., in a neurovascular procedure. Other diameters are contemplated for cardiovascular, peripheral vascular, and gastrointestinal applications. The diameter of the guidewire may remain relatively constant over a major portion of the length of the guidewire; however, the leading or distal end incorporates a generally tapered or narrowed configuration to permit flexure while navigating the tortuous vasculature.

The various embodiments of the disclosure will now be described in connection with the drawing figures. It should be understood that for purposes of better describing the disclosure, the drawings may not be to scale. Further, some of the figures include enlarged or distorted portions for the purpose of showing features that would not otherwise be apparent.

Referring now to FIG. 1, a tortuous vasculature such as within the neurovascular space "n" is illustrated. For illustrative purposes, a tortuous path or a tortuous region within, e.g., the neurovascular space "n", includes large vasculature "v1" and smaller branch vessels "v2" which branch or extend from more proximal vessels at various angles, including up to 90 degrees or even greater than 90 degrees.

In FIG. 1, guidewire 10 of the present disclosure is illustrated as being positioned within a conventional access or microcatheter 100. Such microcatheters are known in the art. One suitable microcatheter is the reinforced microcatheter disclosed in commonly assigned U.S. Pat. No. 7,507,229 to Hewitt et al., the entire contents of which are incorporated by reference herein. In general, microcatheter 100 includes handle 102 and hollow catheter member 104 extending from the handle 102. Microcatheter 100 defines a longitudinal opening extending at least through catheter member 104 for passage or reception of guidewire 10.

Guidewire 10 includes actuator 12 and guide member 14 extending from the actuator 12. Actuator 12 may incorporate various features includes handles, slides or the like, to facilitate handling and/or movement of guide member 14. For example, actuator 12 may be used to translate and/or rotate guide member 14 during placement within the vasculature.

Figure 2:
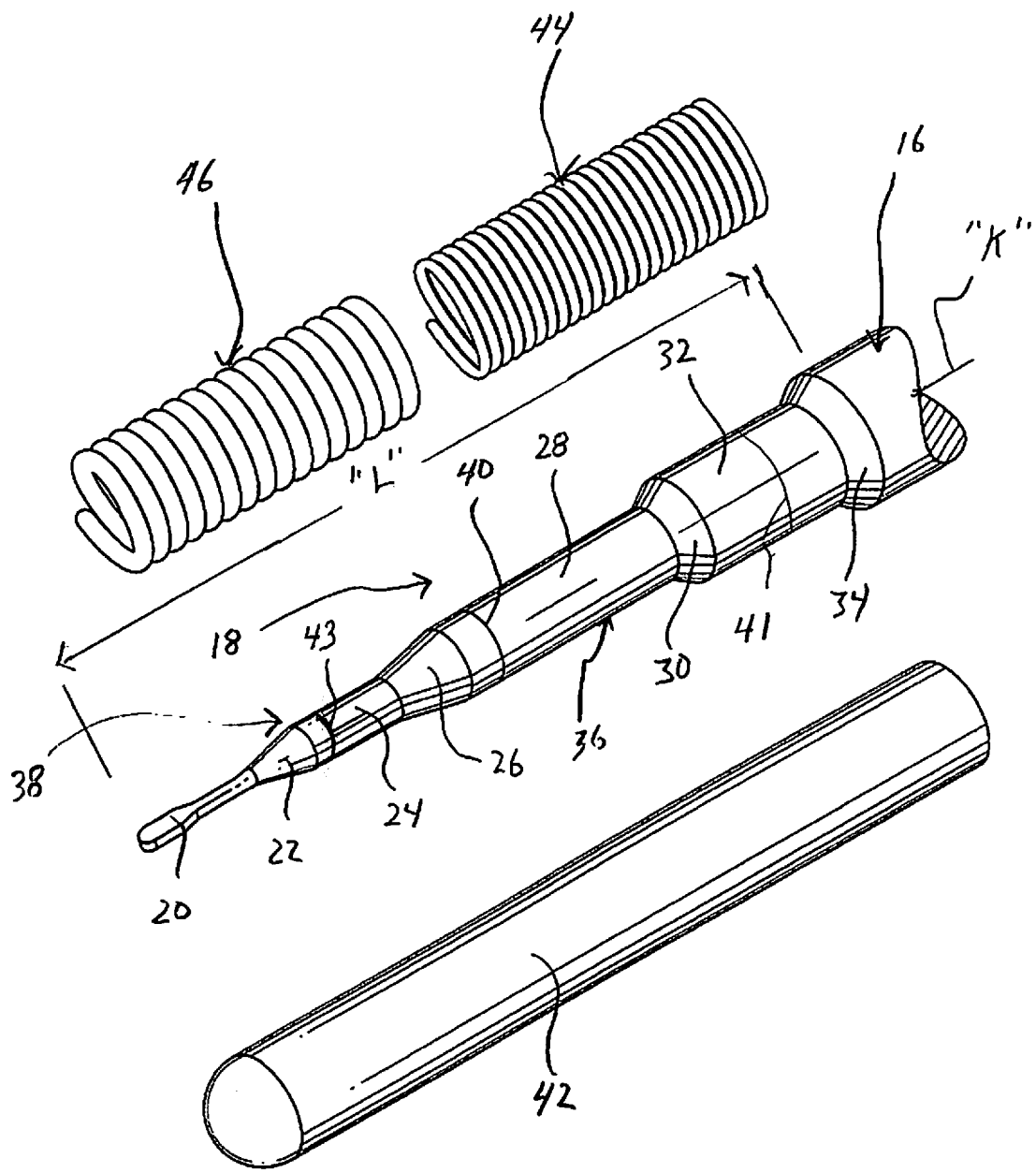
FIG. 2 is a perspective view with parts separated of the guidewire of FIG. 1 illustrating the guide member, support springs and outer sheath.

Referring now to FIG. 2, guide member 14 of guidewire 10 is illustrated and will be discussed in greater detail. Guide member 14 is dimensioned for insertion within the vasculature. Guide member 14 defines longitudinal axis "k" and has proximal or trailing end segment 16 and distal or leading end segment 18 forward of the trailing end segment 16. In FIG. 2, a major longitudinal portion of proximal end segment 16 is removed for ease of illustration. Trailing end segment 16 may be generally circular in cross-section with a length ranging from about 20 cms. to about 240 cms. Trailing end segment 16 may have a constant cross-sectional dimension or diameter along its length.

With reference now to FIGS. 2-3, leading end segment 18 of guide member 14 is the working end or tip of the guidewire 10 and defines a reduced cross-sectional dimension relative to the cross-sectional dimension of proximal end segment 16. The overall length "L" (FIG. 2) of leading end segment 18 may range from about 20 cms to about 60 cms depending on the maximum diameter (e.g., the diameter of proximal end segment 16) and the overall length of guidewire 10. Leading end segment 18 may include a number of alternating tapered and annular segments which generally increase in cross-sectional dimension or diameter from the extreme remote or distal end toward the proximal end, i.e., toward proximal end segment 16. In the embodiment of FIGS. 2-3, leading end segment 18 includes distal remote segment 20, first tapered segment 22 extending from the remote segment 20 and coterminous therewith, first generally annular segment 24 extending from the first tapered segment 22 and coterminous therewith, second tapered segment 26 extending from the first generally annular segment 24 and coterminous therewith, and second generally annular segment 28 extending from the second tapered segment 26 and being coterminous therewith. Leading end segment 18 may further include third tapered segment 30 extending contiguously from second annular segment 28 and third annular segment 32 which is coterminous with the third tapered segment 30. As a further alternative, leading end segment 18 may also include fourth tapered segment 34 extending from third annular segment 32 to leading end segment 16. First, second and third annular segments 24, 28, 32 may define circular cross-sections with various diameters as depicted in the cross-sectional views of FIGS. 4, 5 and 6, respectively. Suitable diameters of each of annular first second and third annular segments 24, 28, 32 for specific guidewire sizes will be provided hereinbelow. Tapered segments 22, 26, 30 and 34 are in oblique relation to the longitudinal axis "k". Tapered segments 22, 26 may define an angle relative to longitudinal axis "k" ranging from about 5 degrees to about 30 degrees. Tapered segments 30, 34 may define a greater angle relative to longitudinal axis "k", e.g., ranging from about 20 degrees to about 70 degrees.

Remote segment 20 may define various configurations. In the embodiment of FIGS. 2-3, remote segment 20 is a flattened, planar or ribbon tip. However, remote segment 20 may define alternative cross-sectional shapes including circular, oval or the like. As a further alternative, remote segment 20 may be heat set into a variety of configurations including a linear arrangement. In one embodiment, remote segment 20 is heat set to maintain, e.g., a non-linear configuration such as a curve, by subjecting the remote segment 20 to heat at about 500° C. to about 525° C. for a duration of time ranging from about 30 seconds to about 2 minutes. Remote segment 20 may also be provided with a bent "j-hook" as is known in the art, or, may be bent into "j-hook" design by the clinician prior to the interventional procedure.

With particular reference to FIG. 3, in conjunction with FIG. 2, in accordance with an embodiment of the disclosure, leading end segment 18 is fabricated from at least two core elements having different core materials with different mechanical properties. For example, first core element 36 encompasses at least a section of second annular segment 28 and extends proximally toward proximal or trailing end segment 16 of guidewire 10, and may encompass the entirety of the trailing end segment 16. Second core element 38 (identified by the different cross-hatching in FIG. 3) is distal or forward of first core element 36 and may encompass the remaining distal section of second annular segment 28, second tapered segment 26, first annular segment 24, first tapered segment 22 and remote segment 20. As will be discussed in detail hereinbelow, first core element 36 and second core element 38 are joined at bond location 40.

Second core element 38 may comprise a shape memory or superelastic alloy or polymer. One suitable shape memory alloy (SMA) or superelastic metal is Nitinol (NiTi), a nickel/titanium alloy, which is commercially available in various diameters or sizes. Superelastic alloys such as NiTi are relatively flexible capable of effectively tracking tortuous vasculature encountered while exhibiting advantageous restoration capabilities. Shape memory or superelastic metal or polymer such as NiTi may also be suitable for applications in which it is desired that leading end segment 18 have a predetermined curvature. Shape memory alloys including NiTi can be heat set into a desired shape, straightened for delivery to a site, and then released to resume the heat-set shape. Other materials for second core element 38 may include an alloy consisting of Nickel, Titanium, and Cobalt commercially available from SAES Smart Materials, Inc, of New Hartford, N.Y.

First core element 36 is preferably fabricated from a more rigid material having a greater elastic modulus, torsional and/or lateral rigidity than the material of second core element 38. In one embodiment, first core element 36 is fabricated from MP35N, a nickel-cobalt alloy. MP35N is a cold worked, age hardenable nickel-cobalt base alloy having a combination of strength, toughness, durability and corrosion resistance. A typical composition of MP35N is 35% Nickel (Ni), 35% Cobalt (CO), 20% Chromium (Cr) and 10% Molybdenum (MO). Wire fabricated from MP35N is commercially available in various diameter sizes from, e.g., Fort Wayne Metals of Fort Wayne, Ind. The more rigid first core element 36 enhances pushability through the vasculature and torque transmission as will be discussed. Other suitable materials for first core element 36 include stainless steel, titanium and alloys thereof, and the Nickel Titanium Cobalt alloy identified hereinabove. The properties of these materials may be altered through the use of additive materials, manufacturing processes or the like to provide the required lateral strength and stiffness to realize the desired characteristics of first core element 36 discussed hereinabove.

First core element 36 may be bonded to second core element 38 at bonding location 40 within second annular segment 28 through various means including bonding, welding, adhesives or the like. In one embodiment, first core element 36 is secured to second core element 38 through a welding process such as a laser or radio frequency (RF) welding process. The welding process contemplated is devoid of filler or bonding materials, thereby providing a direct connection or mating of the elements of first and second core elements 36, 38 during application of heat. The ends of each of first and second core elements 36, 38 to be joined may be subjected to an acid wash to remove impurities, and/or edges prior to welding of the components.

The provision of first and second core elements 36, 38 of different materials having different elastic modulus, rigidities and/or torsional strengths within leading end segment 18, in combination with the dimensioning of the components of the leading end segment 18, provides significant benefits with respect to pushability, lateral strength, torque transfer and flexibility of the guidewire 10. For example, in one embodiment, second core element 38 encompasses about 10% to about 20% of the overall length of leading end segment 18. In embodiments, second core element 38 may extend from remote end 20 a distance "m" (FIG. 3) ranging from about 10 cm to about 20 cm. This localization or provision of the less rigid second core element 38 at the remote end of leading end segment 18 (and/or the relatively increased length of the more rigid first core element 36 within the leading end segment 18) increases pushability of guide member 12 within the tortuous vasculature, improves torque transmission and minimizes distal deformation while also providing sufficient flexibility to accommodate the turns of the vasculature within the neurovascular space. The respective lengths of first and second core elements 36, 38 for various guidewire sizes are outlined in the Table hereinbelow.

As mentioned hereinabove, in the embodiment depicted in FIGS. 2 and 3, first and second core elements 36, 38 are joined at location 40 within second annular segment 28. It is envisioned that the juncture location may be anywhere along leading end segment 18, including, e.g., along second tapered segment 26, third tapered segment 30 or third annular segment 32, e.g., at location 41, or arranged to be bonded within first annular segment 24, e.g., at location 43.

With continued reference to FIGS. 2 and 3, leading end segment 18 further includes at least one coil coaxially mounted about at least a portion of the leading end segment 18, and outer sheath 42. In embodiments, leading end segment 18 includes two coils, namely, first or proximal coil segment 44 and second or distal coil segment 46 forward of the proximal coil segment 44. Proximal coil segment 44 may be fabricated from a number of materials including MP35N discussed hereinabove. Proximal coil segment 44 may be dimensioned to extend to encompass second annular segment 28 and a portion of second tapered segment 26. The diameter of the wire of proximal coil segment 44 may range from about 0.0009 inches to about 0.0025 inches, and, in one embodiment, is about 0.0012 inches. Proximal coil segment 44 may also have a rectangular or flattened cross-section.

Distal coil segment 46 extends from proximal coil segment 44 and encompasses the remainder of leading end segment 18 of guide member 14. Distal coil segment 46 may be fabricated from a number of materials. In one embodiment, distal coil segment 46 is fabricated from the commercially available radiopaque Biomed material sourced by Johnson-Matthey of London, England, and is offered in 3 grades, namely, grade 1400 including 86% Palladium (Pd), 14% Rhenium(Re), grade 1000 including 90% Pd, 10% Re and grade 500 including 95% Pd, 5% Re. The wire of distal coil segment 46 has a diameter greater than the wire of proximal coil segment 44. In one embodiment, the diameter of distal coil segment 46 ranges from about 0.0012 inches to about 0.0025 inches, and may be about 0.0015 inches. Distal coil segment 46 may also have a rectangular or flattened cross-section. The radiopacity of distal coil segment 46 may assist in placement of leading end segment 18 within the vasculature through the use of imaging means, e.g., fluoroscopically during the interventional procedure.

Proximal coil segment 44 and distal coil segment 46 may provide lateral and/or torsional support to leading end segment 18. In one embodiment, the lateral strength (or resistance to bending) of distal coil segment 46 is less than the lateral strength of proximal coil segment 44 to permit flexing of second core element 38 of leading end segment 18. The outer diameters of proximal and distal coil segments 44, 46 may approximate each other and may be substantially equivalent to the diameter of third annular segment 32 to provide a smooth transition. The configurations of proximal and distal coil segments 44, 46 may be changed to provide varied properties if desired. In an embodiment, proximal and distal coil segments 44, 46 may be wound or otherwise disposed about leading end segment 18 in differing or opposite directions. In embodiments, adjacent turns of the coils of each of proximal and distal coil segments 44, 46 are in contacting relation (i.e., they are devoid of spacing between the adjacent coil turns). In one embodiment, proximal and distal coil segments 44, 46 may be joined at their interface. In addition, proximal and distal coil segments 44, 46 may be attached to leading end segment 18 of guide member 14 along various locations. Attachment may be effected though the use of adhesives, welding, soldering or the like. Distal coil segment 46 may be operatively connected or secured to remote end 20 of leading end segment 18 through a soldering process or with the use of an adhesive such as an epoxy, cyanoacrylate adhesive or an ultraviolet (UV) light curable adhesive. The soldering or adhesive element is represented schematically as element 48 in FIG. 3.

Outer sheath 42 encloses leading end segment 18 and proximal and distal coil segments 44, 46. Outer sheath 42 may be fabricated from any suitable material. In one embodiment, outer sheath 42 is a polyurethane sleeve which may or may not be loaded with tungsten, e.g., in microbead form. If loaded with tungsten, outer sheath 42 provides an additional element of radiopacity to leading end segment 18 of guide member 14. Outer sheath 42 may be thermoformed over leading end segment 18 and proximal and distal coil segments 44, 46 through conventional thermoform techniques. Outer sheath 42 defines an atraumatic arcuate leading end surface 50 to minimize the potential of trauma or abrasion of the vessel walls. In one embodiment, the diameter of outer sheath 42 is less than the diameter of proximal or trailing end segment 16 of guide member 14 to provide a smooth transition between the components.

The Table provided below identifies ranges of dimensions of the components of the leading end segment 18 for various guidewire sizes in accordance with the principles of the present disclosure. In the Table, D is represented as a percentage (%) of the diameter of the trailing end segment 16 and L represents the specific length of the component. For example, the diameter of first annular segment 24 may range from about 10% to about 30% of the diameter of trailing end segment 16 and have a length ranging from about 2 cms. to about 10 cms. All ranges are approximate. Preferred dimensions for the specific guidewire sizes may be at the midpoint of the specified ranges. Variations of these dimensions are envisioned. The first core element 36 is fabricated from MP35N and the second core element 38 is fabricated from NiTi. As noted, the overall length of first core element 36 may range from about 10 cms. to about 40 cms. and the overall length of second core element 38 may range from about 20 cms. to about 290 cms.

TABLE

|  | 1$^{st}$ Annular Segment 24 | 2nd Annular Segment 28 | 3$^{rd}$ Annular Segment 32 | First Core Element 36 | Second Core Element 38 |
|---|---|---|---|---|---|
| D (%) | 10-30% | 25-50% | 50-90% | | |
| L (cms.) | 2-10 cms. | 5-30 cms. | 10-30 cms. | 10-40 cms. | 20-290 cms. |

It is further envisioned that a lubricious coating may be disposed over components of guide member 14 including outer sheath 42. Suitable lubricious coatings include hydrophilic materials such as polyvinylpyrrolidone (PVP), polyethylene oxide, polyethylene glycol, cellulosic polymers, and hydrophilic maleic anhydride, or hydrophobic materials such as silicone, PTFE, or FEP. These coatings are typically applied by dip coating or spray methods, and heat curing may be used. For example, cure temperatures up to about 70 degrees C. are used for silicone coatings, and several hundred degrees may be required for PTFE coatings. In addition to the lubricious coating, bioactive coatings may be applied over all or part of the guidewire. Such coatings also may incorporate materials such as heparin, hirudin and its analogs, or other drugs. These coatings typically are applied by dip coating. Bioactive coatings are desirable to prevent blood clotting or for delivery of drugs to a specific site.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A guidewire for use in a medical procedure, the guidewire comprising:
  an elongate guide member dimensioned for insertion within a body vessel of a subject, the guide member defining a longitudinal axis and comprising a trailing end segment and a leading end segment, the leading end segment having a reduced cross-sectional dimension relative to a cross-sectional dimension of the trailing end segment, the leading end segment including:
    a first core element comprising a first material; and
    a second core element comprising a second material different from the first material, the second core element being forward of the first core element,
    wherein a proximal end of the second core element is directly bonded to a distal end of the first core element such that the second material of the second core element is directly bonded to the first material of the first core element, the first material of the first core element having greater rigidity than the rigidity of the second material of the second core element, to thereby facilitate advancement of, and application of torque to, the leading end segment while minimizing deformation of the elongate guide member; and
  a coil member coaxially mounted about the guide member and dimensioned to longitudinally extend to at least partially encompass and engage with each of the first and second core elements.

2. The guidewire according to claim 1 wherein the first material of the first core element comprises a nickel-cobalt-chromium alloy.

3. The guidewire according to claim 1 wherein the first material of the first core element comprises stainless steel.

4. The guidewire according to claim 2 wherein the second material of the second core element comprises an alloy including nickel and titanium.

5. The guidewire according to claim 1 wherein the first core element is bonded to the second core element through a welding process, the welding process devoid of any filler material.

6. The guidewire according to claim 1 wherein the coil member includes a first coil segment and a second coil segment forward of the first coil segment.

7. The guidewire according to claim 6 wherein the first coil segment comprises a first coil material and the second coil segment comprises a second coil material different from the first coil material.

8. The guidewire according to claim 6 wherein the first coil segment has a first torsional strength and the second coil segment has a second torsional strength greater than the first torsional strength.

9. The guidewire according to claim 1 wherein the leading end segment includes at least two tapered segments obliquely arranged with respect to the longitudinal axis.

10. The guidewire according to claim 9 wherein the leading end segment includes, from leading to trailing:
   a remote segment;
   a first tapered segment extending from the first remote segment and coterminous therewith;
   a first generally annular segment extending from the first tapered segment and coterminous therewith;
   a second tapered segment extending from the first generally annular segment and coterminous therewith; and
   a second generally annular segment extending from the second tapered segment and coterminous therewith.

11. The guidewire according to claim 10 wherein the first core element is connected to the second core element within the second generally annular segment.

12. The guidewire according to claim 10 wherein the first core element is connected to the second core element within a third generally annular segment that extends from a third tapered segment, the third tapered segment extending from the second generally annular segment.

13. The guidewire according to claim 10 wherein the remote segment defines one of a polygonal or annular cross-section.

14. The guidewire according to claim 10 wherein the remote segment is heat set into a predetermined configuration.

15. The guidewire according to claim 14 wherein the predetermined configuration is generally arcuate.

16. The guidewire according to claim 1 including a sleeve mounted over at least a major portion of the leading end segment.

17. The guidewire according to claim 16 wherein the sleeve comprises polyurethane and tungsten material.

18. The guidewire according to claim 16 wherein the sleeve defines an arcuate distal tip.

19. The guidewire according to claim 1 wherein the first and second core elements do not overlap in an axial direction, the axial direction extending parallel to along a longitudinal axis of the elongate guide member.

20. The guidewire according to claim 1 wherein a portion of the second material of the second core element axially adjacent to the first material of the first core element is directly bonded to the first material of the first core element.

* * * * *